(12) United States Patent
Coulton et al.

(10) Patent No.: US 6,274,594 B1
(45) Date of Patent: Aug. 14, 2001

(54) ISOQUINOLINE DERIVATIVES AND THEIR THERAPEUTICAL USE

(75) Inventors: Steven Coulton, Horsham; Roderick Alan Porter, Near Baldock; Mervyn Thompson, Harlow, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/554,569

(22) PCT Filed: Nov. 16, 1998

(86) PCT No.: PCT/EP98/07520

§ 371 Date: May 16, 2000

§ 102(e) Date: May 16, 2000

(87) PCT Pub. No.: WO99/25709

PCT Pub. Date: May 27, 1999

(30) Foreign Application Priority Data

Nov. 18, 1997 (GB) .................................................. 9724372

(51) Int. Cl.⁷ ........................ A61K 31/47; C07D 217/02; C07D 217/22

(52) U.S. Cl. .......................... 514/308; 514/310; 546/140; 546/143

(58) Field of Search ..................................... 514/308, 310; 546/140, 143

(56) References Cited

FOREIGN PATENT DOCUMENTS

| WO93/18028 | 9/1993 | (GB) . |
| WO94/04533 | 3/1994 | (GB) . |
| WO96/39382 | 12/1996 | (JP) . |
| WO94/22871 | 10/1994 | (WO) . |

*Primary Examiner*—D. Margaret Seaman
(74) *Attorney, Agent, or Firm*—Soma G. Simon; William T. King; Charles M. Kinzig

(57) ABSTRACT

Novel isoquinoline derivatives and methods of using them to treat various neurological indications are disclosed.

8 Claims, No Drawings

ISOQUINOLINE DERIVATIVES AND THEIR THERAPEUTICAL USE

This invention relates to novel compounds, to processes for preparing them, and to their use as therapeutic agents.

WO96/39382 (Fujisawa) discloses the preparation of N-heterocyclyl-ureas as 5-HT antagonists, including the compound N-(1-methyl-1H-indol-5-yl)-N'-(1,2,3,4-tetrahydro-7-isoquinolinyl)-urea.

It has now been surprisingly found that heterocyclyl-N-carboxamide compounds of formula (I) below possess anti-convulsant activity and are therefore believed to be useful in the treatment and/or prevention of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, panic disorders and/or aggression.

Accordingly, the present invention provides a compound of formula (I) or pharmaceutically acceptable salt thereof:

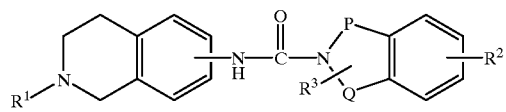

(I)

where P and Q are each independently a bond, methylene or ethylene such the ring structure Z is a five or six membered ring, $R^1$ is hydrogen or $C_{1-6}$ alkyl, $R^2$ is hydrogen or up to four substituents independently selected from halogen,
$CF_3$, $NO_2$, CN, $N_3$, $C_{1-6}$ alkylO—, $C_{1-6}$ alkylS—, $C_{1-6}$ alkyl, $C_{3-6}$ cycloalkyl,
$C_{3-6}$cycloalkyl-$C_{1-4}$alkyl-, $C_{1-6}$alkenyl, $C_{1-6}$alkynyl, $CF_3CO$—, $CF_3O$,
$C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-,
or —$NR^4R^5$ where
$R^4$ is hydrogen or $C_{1-4}$ alkyl, and
$R^5$ is hydrogen, $C_{1-4}$alkyl, —CHO, —$CO_2C_{1-4}$alkyl or —$COC_{1-4}$alkyl.

$R^3$ is hydrogen or up to two $C_{1-6}$ alkyl groups.

The ring structure Z is a five or six-membered saturated ring, optionally substituted by one or two $C_{1-6}$alkyl groups, including gem-dialkyl substitution, typically such that compounds of this invention are tetrahydroisoquinoline, tetrahydroquinoline or dihydroindole N-carboxamides.

The left hand side tetrahydroisoquinolinyl moiety is typically tetrahydroisoquinolin-5-yl or tetrahydroisoquinolin-7-yl.

The benzene ring fused to ring structure Z may be substituted by up to four, preferably 2 or 1, non-hydrogen $R^2$ groups.

In the formula (I), alkyl groups, including alkyl groups that are part of another moiety, may be straight chain or branched. Aromatic rings, such as the aromatic ring in the bicyclic heterocyclic moiety in formula (I) and phenyl groups, including phenyl groups that are part of other moieties, in $R^2$ may optionally be substituted with one or more independently selected halogen or $C_{1-6}$ alkyl, $C_{1-6}$ alkoxy or $C_{1-6}$ alkylcarbonyl.

Suitable $C_{3-6}$ cycloalkyl groups include cyclopropyl, cyclobutyl, cyclopentyl, and cyclohexyl.

Suitable halo substituents include fluoro, chloro, iodo and bromo.

A suitable group of compounds of formula (I) have substituents selected from:
$R^1$ as hydrogen, methyl, ethyl or propyl,
$R^2$ as hydrogen, methyl, ethyl, n-butyl, phenyl, iso-propyl, t-butyl, methoxy, ethoxy, n-propoxy, iso-propoxy, n-butoxy, phenoxy, benzyloxy, bromo, chloro, iodo, fluoro, nitro, cyano, acetyl, pivaloyl, iso-butyroyl, benzoyl, trifluoromethyl, trifluoromethoxy, trifluoroacetyl, amino, acetylamino, methylthio, n-propylsulfonyl, isopropylsulfonyl or dimethylsulfamoyl.
$R^3$ as hydrogen or methyl.

Examples of compounds of formula (I) are:
2,3-dihydroindole-1-carboxylic acid (2-methyl-1,2,3,4-tetrahydroisoquinolin-7-yl)amide
3,4-dihydro-1H-isoquinoline-2-carboxylic acid (2-methyl-1,2,3,4-tetrahydro-isoquinolin-7-yl)amide
3,4-dihydro-2H-quinoline-1-carboxylic acid (2-methyl-1,2,3,4-tetrahydro-isoquinolin-7-yl)amide
2,3-dihydro-5-methylthio-6-trifluoromethyl-indole-1-carboxylic acid (2-methyl-1,2,3,4-tetrahydroisoquinolin-5-yl)amide
2,3-dihydro-6-methoxyindole-1-carboxylic acid (2-methyl-1,2,3,4-tetrahydro-isoquinolin-7-yl)amide
2,3-dihydro-4-methoxyindole-1-carboxylic acid (2-methyl-1,2,3,4-tetrahydro-isoquinolin-7-yl)amide
2,3-dihydro-4,5,6,7-tetrafluoroindole-1-carboxylic acid (2-methyl-1,2,3,4-tetrahydroisoquinolin-7-yl)amide
2,3-dihydro-5-fluoroindole-1-carboxylic acid (2-methyl-1,2,3,4-tetrahydro-isoquinolin-7-yl)amide
2,3-dihydro-5-nitroindole-1-carboxylic acid (2-methyl-1,2,3,4-tetrahydro-isoquinolin-7-yl)amide
2,3-dihydro-6-nitroindole-1-carboxylic acid (2-methyl-1,2,3,4-tetrahydro-isoquinolin-7-yl)amide
2,3-dihydro-5-methoxy-6-trifluoromethylindole-1-carboxylic acid (2-methyl-1,2,3,4-tetrahydroisoquinolin-7-yl)amide
3,3-dimethyl-2,3-dihydroindole-1-carboxylic acid (2-methyl-1,2,3,4-tetrahydro-isoquinolin-7-yl)amide
2,3-dimethyl-2,3-dihydroindole-1-carboxylic acid (2-methyl-1,2,3,4-tetrahydro-isoquinolin-7-yl)amide
2,3-dimethyl-2,3-dihydroindole-1-carboxylic acid (2-methyl-1,2,3,4-tetrahydro-isoquinolin-7-yl)amide
3,3-dimethyl—5-fluoro-2,3-dihydroindole-1-carboxylic acid (2-methyl-1,2,3,4-tetrahydro-isoquinolin-7-yl)amide.

When synthesised, these compounds may be in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above-listed compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, nasal, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, in a further aspect, the present invention provides a pharmaceutical composition for use in the treatment and/or prophylaxis of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, panic disorders and/or aggression which comprises a compound of formula (I), or a pharmaceutically acceptable salt or solvate thereof, and a pharmaceutically acceptable carrier.

The present invention also provides a method of treatment and/or prophylaxis of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic, epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, panic disorders and/or aggression comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, panic disorders and/or aggression.

In a further aspect the invention provides the use of a compound of formula (I), or a pharmaceutically acceptable salt or solvate, thereof as a therapeutic agent, in particular for the treatment and/or prophylaxis of anxiety, mania, depression disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, panic disorders and/or aggression.

Another aspect of the invention provides a process for the preparation of compounds of formula (I), which comprises reacting a compound of formula (II)

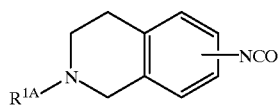

(II)

where $R^{1A}$ is $R^1$ as defined for formula (I) or a group convertible to $R^1$, with a compound of formula (III)

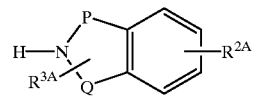

(III)

where P, Q and Z are as defined for formula (I), and $R^{2A}$, $R^{3A}$ are $R^2$, $R^3$ as defined for formula (I) or a group or groups convertible to $R^2$, $R^3$
and where required converting a $R^{1A}$, $R^{2A}$ or $R^{3A}$ group to a $R^1$, $R^2$ or $R^3$ group, converting one $R^1$, $R^2$ or $R^3$ group to another $R^1$, $R^2$ or $R^3$ group, converting a salt product to the free base or another salt which is pharmaceutically acceptable, or converting a free base product to a pharmaceutically acceptable salt.

Typically the ring structure Z is selected so that compounds of formula (III) are optionally substituted tetrahydroisoquinolines, tetrahydroquinolines or dihydroindoles.

Conversions of a $R^{1A}$, $R^{2A}$ or $R^{3A}$ group to a $R^1$, $R^2$ or $R^3$ group typically arise when a protecting group is needed during the above coupling reaction or during the preparation of the reactants by the procedures described below. Interconversion of one $R^1$, $R^2$ or $R^3$ group to another typically arises when one compound of formula (I) is used as the immediate precursor of another compound of formula (I), or when it is easier to introduce a more complex or reactive substituent at the end of a synthetic sequence.

Conventional conditions for condensation of isocyanates with amines may be used, for example treatment in an inert solvent such as toluene, DMF or dichloromethane at ambient or elevated temperature.

Compounds of formula (II) may be prepared from the corresponding amines using conventional procedures such as described by I T Forbes et al, J. Med. Chem., 1993, 36, 1104, and in Fieser and Fieser, Reagents for Organic Synthesis Vol I. For example an isocyanate may be prepared by stirring a relevant amine with one equivalent of carboxyl diimidazole in a suitable solvent such as dichloromethane at room temperature, and then evaporated to dryness in vacuo.

The amine precursor of formula (II) may be prepared from the corresponding unsaturated compound of formula (IV)

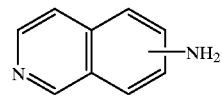

(IV)

by reaction with a compound $R^{1A}Z$ where Z is a leaving group such as halogen, especially iodo, or tosylate to obtain an intermediate of formula (V)

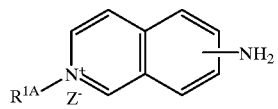

(V)

which can be reduced, for example using sodium borohydride, to the compound of formula (II). Alternatively the compound of formula (V) can be hydrogenated, for example using hydrogen at 50 psi in a solution of acetic/sulphuric acid with a platinum oxide catalyst.

Another route is from a precursor of formula (VI)

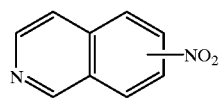

(VI)

which can be reacted with $R^{1A}Z$, preferably as a tosylate, to obtain the intermediate of formula (VII)

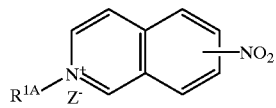

(VII)

which can then be hydrogenated under the conditions previously described.

Compounds of formulae (IV) and (VI) and the reagents used are commercially available, or can be prepared from commercially available materials using conventional procedures described in the literature.

Alternatively, the amine precursor may be prepared directly from the corresponding nitro compound by catalytic hydrogenation. More specifically 7-amino-tetrahydroisoquinolines may be prepared by the procedure of G E Stokker, Tet. Lett. 1996, 37, 5453.

When $R^{1A}$ is hydrogen, the amine precursor of the compound of formula (II) can be obtained by direct hydrogenation of the compounds of formula (IV) or (VI), using the reagents already described. The NH may be protected conventionally, for example by making $R^{1A}$ t-butoxycarbonyl, prior to formation of the carboxamide, and then deprotected under standard conditions, for example using trifluoroacetic acid/methylene chloride.

Compounds of formula (III) are commercially available or may be prepared by conventional manipulation of substituents on commercially available substituted heterocyclic compounds. Alternatively, compounds of formula (III) may be synthesised by conventional procedures for preparation of tetrahydroisoquinoline, tetrahydroquinoline or dihydroindole compounds with desired substituents in situ. For example ring-closing reactions between substituted alkene chlorides and substituted anilines may be used, analogous to those set out in the Descriptions below.

The preparation of intermediates and starting materials for the process of this invention is illustrated by the following Descriptions; the preparation of compounds of this invention is illustrated by the following Examples. The utility of compounds of this invention is shown by the Pharmacological Data that follow the Examples.

Description 1
N-2-(4-Nitrophenyl)ethyl-trifluoroacetamide

A solution of trifluoroacetic anhydride (10.6 ml) in dichloromethane (100 ml) was added dropwise to a stirred solution of 2,6-lutidine (17.44 ml) and 4-nitrophenethylamine hydrochloride (15.2 g; 75 mmol) at 0° C. The mixture was stirred at 25° C. overnight under argon and then washed with dilute citric acid (x2), brine and dried over $Na_2SO_4$. The material in the organic phase gave the title compound as a pale yellow solid (19.04 g).

Description 2
7-Nitro-1,2,3,4-tetrahydro-2-trifluoroacetyl-isoquinoline

The nitro compound D1 (2.26 g; 9.15 mmol) and paraformaldehyde (0.45 g; 14.4 mmol) in acetic acid (10 ml) and conc. $H_2SO_4$ (15 ml) were stirred at 25° C. for 20 h according to the procedure of G. E. Stokker., Tet. Lett., 1996, 37, 5453. Work up afforded the title compound as a white solid (2.17g).

$^1$H NMR (CDCl$_3$) δ: 3.10 (2H, m), 3.92 (2H, m), 4.85+ 4.92 (2H, 2xs), 7.38 (1H, t), 8.10 (2H, m); $m/z$ (EI): 274 (M$^+$).

Description 3
7-Nitro-1,2,3,4-tetrahydroisoquinoline

The trifluoroacetamide D2 (17.22 g; 63 mmol) was hydrolysed at room temperature using a solution of potassium carbonate (46.6 g) in 10% aqueous methanol (660 ml). Work-up with dichloromethane gave the title compound (11 g).

Description 4
2-Methyl-7-nitro-1,2,3,4-tetrahydroisoquinoline

The amine D3 (2.08 g; 11.7 mmol) was treated with 88% formic acid (3.45 ml) and 37% aqueous formaldehyde (5.88 ml) at 80° C. for 2 h according to the procedure of G. M. Carrera and D. S. Garvey, J. Het. Chem., 1992, 29, 847. Basification with 10% sodium hydroxide followed by work-up with ethyl acetate afforded an orange gum (2.3 g). Chromatography on Kiesegel 60 in 0–3% methanol-ethyl acetate gave the title compound as an orange solid (1.7 g).

$m/z$ (CI):193 (MH$^+$).

Description 5
7-Amino-2-methyl-1,2,3,4-tetrahydroisoquinoline

The 7-nitro compound D4 (0.25 g; 1.3 mmol) in methanol (40 ml) was hydrogenated over 10% palladium on carbon (100 mg) at atmospheric pressure overnight. The catalyst was removed by filtration through a pad of Kieselguhr and evaporation in vacuo gave the title compound as a white solid (213 mg).

$m/z$ (CI): 163 (MH$^+$).

Description 6
2-Methyl-1,2,3,4-tetrahydroisoquinoline-7-isocyanate

The amine D5 (245 mg, 1.5 mmol) and carbonyldiimidazole (243 mg, 1.5 mmol) in dichloromethane (10 ml) were stirred at 25° C. for 1 h and then evaporated to dryness in vacuo.

Description 7
5-Amino-2-methylisoquinolinium Iodide

To a solution of 5-aminoisoquinoline (14.4 g, 100 mmol) in acetone (300 ml) was added iodomethane (14.4 ml). The solution was briefly stirred and then allowed to stand for 2 h. The yellow precipitate was then filtered, washed with acetone and dried to afford the title compound as a yellow solid (18.8 g).

Description 8
5-Amino-2-methyl-1,2,3,4-tetrahydroisoquinoline

Sodium borohydride (17.8 g, 0.47 mol) was added portionwise over 2 h to an ice cold solution of 5-amino-2-methylisoquinolinium iodide (18.8 g, 65 mmol) in methanol (1.5 L) and water (60 ml). The mixture was then stirred at 25° C. for 18 h. and concentrated in vacuo. The residue was extracted into water and dichloromethane. The organic layer was dried (Na$_2$SO$_4$) and concentration in vacuo gave the title compound (8.87 g).

Description 9
2-Methyl-1,2,3,4-tetrahydroisoquinoline-5-isocyanate

The title compound was prepared from amine D8, using a method similar to that of Description 6.

Description 10
N-(2-Methyl-2-propenyl)-N-4-fluoroaniline

A mixture of 4-fluoroaniline (16.7 g) and methallyl chloride (11 g) was stirred in dimethylformamide (50 ml) containing potassium carbonate (16 g) for 48 hrs. The reaction mixture was filtered absorbed onto silica gel and column chromatographed petroleum ether then 8% dichloromethane petroleum ether to give the title compound (13.0 g).

m/z (API+): 166 (MH+; 100%).

Description 11

N-(2-Methyl-2-propenyl)-N-4-fluoroacetanilide

N-(2-methyl-2-propenyl)-N-4-fluoroaniline (8.3 g) in dichloromethane was stirred with 4A molecular sieves (1 g) 4-dimethylaminopyridine (0.2 g) and acetic anhydride (5 mls) overnight. The reaction mixture was filtered and washed with water. The organic phase was separated dried, (MgSO4) and solvent removed at reduced pressure to give the title compound(11.2 g)

m/z (API+): 208 (MH+; 100%)

Description 12

5-Fluoro-3,3-gem-dimethylindoline

Aluminium trichloride (1.4 g) was suspended in chlorobenzene (8 ml) and warmed at 95° C. for 1 hr. N-(2-methyl-2-propenyl)-N-4-fluoroacetanilide (1.0 g) in chlorobenzene (5 ml) was added dropwise under argon. The mixture was stirred for 4 hrs, diluted with toluene (20 ml) and poured onto ice (80 g). The mixture was stirred for 1 hr, the organic phase separated, washed with water, dried (MgSO4) solvent removed at reduced pressure. The residue was column chromatographed (silica gel, dichloromethane/petroleum ether (1:3)) to give the title compound (0.14 g).

m/z (API+): 165 (MH+; 100%)

$^1$H NMR (250 MHz, CDCl$_3$) δ 1.29(6H, s), 3.12(2H, s), 3.59(br. s., 1H), 5.19(1H, dd) and 6.66–6.76(2H, m).

EXAMPLE 1

2,3-Dihydroindole-1-carboxylic Acid (2-methyl-1,2,3,4-tetrahydroisoquinolin-7-yl)amide The residue from Description 6 was dissolved in DMF (10 ml), indoline (0.166 ml; 1.5 mmol) was added and the mixture was heated at 100° C. for 0.5 h. The mixture was cooled and partitioned between ethyl acetate and water. The organic phase was washed with water and brine then dried over sodium sulfate and the solvent was removed in vacuo. Chromatography on SiO$_2$ in 40–100% hexane-ethyl acetate gave the title compound in 77% yield as a colourless gum (353 mg).

$^1$H NMR (250 MHz, CDCl$_3$) δ: 2.42 (3H, s), 2.64 (2H, t, J=6 Hz), 2.84 (2H, t, J=6 Hz), 3.15 (2H, t, J=9 Hz), 3.51 (2H, s), 3.98 (2H, t, J=9 Hz), 6.57 (1H, s), 6.87–7.04 (2H, bm), 7.10–7.26 (4H, bm), 7.89 (1H, d, J=8 Hz); m/z (API+): 308 (MH+; 100%).

EXAMPLE 2

3,4-Dihydro-1H-isoquinoline-2-carboxylic Acid (2-methyl-1,2,3,4-tetrahydriosoquinolin-7-yl)amide The title compound was prepared in 63% yield from isocyanate D6 and 1,2,3,4-tetrahydroisoquinoline using a method similar to that of Example 1.

$^1$H NMR (250 MHz, CDCl$_3$) δ: 2.43 (3H, s), 2.65 (2H, t, J=6 Hz), 2.80–2.95 (4H, bm), 3.52 (2H, s), 3.70 (2H, t, J=6 Hz), 4.64 (2H, s), 6.49 (1H, s), 6.96–7.24 (7H, bm);

m/z (API+): 322 (MH+; 100%)

EXAMPLE 3

3,4-Dihydro-2H-quinoline-1-carboxylic Acid (2-methyl-1,2,3,4-tetrahydroisoquinolin-7-yl)amide The title compound was prepared in 70% yield from isocyanate D6 and 1,2,3,4-tetrahydroquinoline, using a method similar to that of Example 1.

$^1$H NMR (250 MHz, CDCl$_3$) δ: 1.98 (2H, dt, J=6 Hz), 2.44 (3H, s), 2.66 (2H, t, J=6 Hz), 2.75–2.90 (4H, bm), 3.54 (2H, s), 3.82 (2H, t, J=6 Hz), 6.93–7.37 (8H, bm);

m/z (API+): 322 (MH+; 100%)

EXAMPLE 4

2,3-Dihydro-5-methylthio-6-trifluoromethyl-indole-1-carboxylic Acid (2-methyl-1,2,3,4-tetrahydroisoquinolin-5-yl)amide The title compound was prepared from isocyanate D9 and 2,3-dihydro-5-methylthio-6-trifluoromethyl-indole, using a method similar to that of Example 1.

m/z (API+): 422 (MH+; 100%)

EXAMPLE 5

2,3-Dihydro-6-methoxyindole-1-carboxylic Acid (2-methyl-1,2,3,4-tetrahydroisoquinolin-7-yl)amide The title compound was prepared in 37% yield from isocyanate D6 and 6-methoxy-2,3-dihydroindoline, using a method similar to that of Example 1.

$^1$H NMR (250 MHz, CDCl$_3$) δ 2.44(s, 3H), 2.67(t, 2H), 2.87(2H, t), 3.14(2H, t), 3.56(2H, s), 3.80(3H, s), 4.05(2H, t), 6.40(s, 1H), 7.02–7.14(m, 3H), 7.19(s, 1H) and 7.61(d, 1H).

m/z (API+): 338 (MH+; 100%)

EXAMPLE 6

2,3-Dihydro-4-methoxyindole-1-carboxylic Acid (2-methyl-1,2,3,4-tetrahydroisoquinolin-7-yl)amide The title compound was prepared in 46% yield from isocyanate D6 and 4-methoxy-2,3-dihydroindoline, using a method similar to that of Example 1.

$^1$H NMR (250 MHz, d$^6$-DMSO) δ 2.35(3H, s), 2.60(2H, br. s), 2.76(2H, br. s.), 3.03(2H, t), 3.46(2H, s), 3.78(3H, s), 4.10(2H, t), 6.57(1H, d), 6.99–7.30(4H, m), 7.49(1H, d) and 8.37(d, 1H).

m/z (API+): 338 (MH+; 100%)

EXAMPLE 7

2,3-Dihydro-4,5,6,7-tetrafluoroindole-1-carboxylic Acid (2-methyl-1,2,3,4-tetrahydroisoquinolin-7-yl)amide The title compound was prepared in 17% yield from isocyanate D6 and 4,5,6,7-tetrafluoro-2,3-dihydroindoline, using a method similar to that of Example 1.

$^1$H NMR (250 MHz, CDCl3) δ 2.44(3H, s), 2.67(2H, t), 2.88(2H, t), 3.17(2H, t), 3.54(2H, s), 4.24(2H, t), 6.78(1H, d), 7.03–7.14 (2H, m) and 7.18(1H, s)

m/z (API+): 380 (MH+; 100%)

EXAMPLE 8

2,3-Dihydro-5-fluoroindole-1-carboxylic Acid (2-methyl-1,2,3,4-tetrahydroisoquinolin-7-yl)amide The title compound was prepared in 10% yield from isocyanate D6 and 5-fluoro-2,3-dihydroindoline, using a method similar to that of Example 1.

$^1$H NMR (250 MHz, CDCl3) δ 2.45(3H, s), 2.67(2H, t), 2.87(2H, t), 3.22(2H, t), 3.56(2H, s), 4.08(2H, t), 6.30(1H, s), 6.84–6.90(2H, m), 7.03–7.13 (2H, m), 7.20(1H, s) and 7.88(1H, m)

m/z (API+): 326 (MH+; 100%)

EXAMPLE 9

2,3-Dihydro-5-nitroindole-1-carboxylic Acid (2-methyl-1,2,3,4-tetrahydroisoquinolin-7-yl)amide The title compound was prepared in 43% yield from isocyanate D6 and 5-nitro-2,3-dihydroindoline, using a method similar to that of Example 1.

¹H NMR (250 MHz, CDCl3) δ 2.45(3H, s), 2.68(2H, t), 2.89(2H, t), 3.37(2H, t), 3.57(2H, s), 4.19(2H, t), 6.44(1H, s), 7.06–7.15(2H, m), 7.20(1H, s) 8.04(1H, s) and 8.07–8.15 (2H, m)

m/z (API⁺): 353 (MH⁺; 100%)

EXAMPLE 10
2,3-Dihydro-6-nitroindole-1-carboxylic Acid (2-methyl-1,2,3,4-tetrahydro-isoquinolin- 7-yl)amide The title compound was prepared in 43% yield from isocyanate D6 and 6-nitro-2,3-dihydroindoline, using a method similar to that of Example 1.

¹H NMR (250 MHz, CDCl3) δ 2.45(3H, s), 2.68(2H, t), 2.89(2H, t), 3.34(2H, t), 3.57(2H, s), 4.17(2H, t), 6.36(1H, s), 7.05–7.15(2H, m), 7.26(2H, m) 7.84(1H, dd) and 8.81 (1H, d).

m/z (API⁺): 353 (MH⁺; 100%)

EXAMPLE 11
2,3-Dihydro-5-methoxy-6-trifluoromethylindole-1-carboxylic Acid (2-methyl-1,2,3,4-tetrahydroisoquinolin-7-yl)amide The title compound was prepared in 20% yield from isocyanate D6 and 2,3-Dihydro-5-methoxy-6-trifluoromethylindoline, using a method similar to that of Example 1.

¹H NMR (250 MHz, CDCl3) δ 2.44(3H, s), 2.67(2H, t), 2.87(2H, t.), 3.26(2H, t), 3.56(2H, s), 3.85(3H, s), 4.07(2H, t), 6.27(1H, s), 6.85(1H, s), 7.03–7.09(2H, m), 7.19(1H, s) and 8.22(1H, d).

m/z (API⁺): 406 (MH⁺; 100%)

EXAMPLE 12
3,3-Dimethyl-2,3-dihydroindole-1-carboxylic Acid (2-methyl-1,2,3,4-tetrahydroisoquinolin-7-yl)amide The title compound was prepared in 16% yield from isocyanate D6 and 3,3-dimethyl-2,3-dihydroindoline, using a method similar to that of Example 1.

¹H NMR (250 MHz, CDCl3) δ 1.38(6H, s), 2.45(3H, s), 2.67(2H, t), 2.87(2H, t.), 3.57(2H, s), 3.87(2H, s), 6.42(1H, s), 6.96–7.26 (6H, m) and 7.87(1H, d).

m/z (API⁺): 336 (MH⁺; 100%)

EXAMPLE 13
2,3-Dimethyl-2,3-dihydroindole-1-carboxylic Acid (2-methyl-1,2,3,4-tetrahydroisoquinolin-7-yl)amide (3:1 trans:cis)

The title compound was prepared in 55% yield from isocyanate D6 and 2,3-dimethyl-2,3-dihydroindo line (3:1 trans:cis), using a method similar to that of Example 1.

¹H NMR (250 MHz, CDCl₃) δ 1.27(3H, d), 1.39(3H, d), 2.45(3H, s), 2.67(2H, br. s.), 2.88(3H, br. s.), 3.57(2H, s), 4.07(1H, m), 6.62 (1H, s), 6.99–7.25(6H) and 7.66(d, 1H).

m/z (API⁺): 336 (MH⁺; 100%)

EXAMPLE 14
2,3-Dimethyl-2,3-dihydroindole-1-carboxylic Acid (2-methyl-1,2,3,4-tetrahydroisoquinolin-7-yl)amide (1:2 trans:cis)

The title compound was prepared in 55% yield from isocyanate D6 and 2,3-dimethyl-2,3-dihydroindoline (1:2 trans:cis), using a method similar to that of Example 1.

¹H NMR (250 MHz, CDCl₃) δ 1.21(3H, d), 1.32(3H, d), 2.45(3H, s), 2.67(2H, br. s.), 2.87(2H, br. s.), 3.57(3H, br. s), 4.57(1H, m), 6.66 (1H, s), 6.99–7.25(6H) and 7.58(d, 1H).

m/z (API⁺): 336 (MH⁺; 100%)

EXAMPLE 15
3,3-Dimethyl-5-fluoro-2,3-dihydroindole-1-carboxylic Acid (2-methyl-1,2,3,4-tetrahydroisoquinolin-7-yl)amide The title compound was prepared in 30% yield from isocyanate D6 and 3,3-dimethyl-5-fluoro-2,3-dihydroindoline (description 12), using a method similar to that of Example 1.

¹H NMR (250 MHz, CDCl3) δ 1.39(6H, s), 2.45(3H, s), 2.67(2H, t), 2.87(2H, t.), 3.57(2H, s), 3.81(2H, s), 6.29(1H, s), 6.81–6.91 (2H, m) 7.04–7.14(2H, m), 7.22(1H, s) and 7.87(1H, dd).

m/z (API⁺): 3354 (MH⁺; 100%)

Pharmacogical Data

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active in this test with pKi values greater than 6. For example, the compound of Example 1 gave a pKi value greater than 8.

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method for Mouse Model

Mice (naive male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Method for Rat Model

The threshold for maximal (tonic hindlimb extension) electroshock seizures in male rats (Sprague Dawley, 80–150 g, 6 weeks old) was determined by a Hugo Sachs Electronik stimulator which delivered a constant current (0.3 sec duration; from 1–300 mA in steps of 5–20 mA). The procedure is similar to that outlined above for mouse and full details are as published by Upton et al,.[4]

The percentage increase or decrease in $CC_{50}$ for each group compared to the control is calculated.

Drugs are suspended in 1% methyl cellulose.

REFERENCES

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113
4. N. Upton, T. P. Blackburn, C. A. Campbell, D. Cooper, M. L. Evans, H. J. Herdon, P. D. King,
5. A. M. Ray, T. O. Stean, W. N. Chan, J. M. Evans and M. Thompson. (1997). B. J. Pharmacol., 121, 1679–1686.

Results for Rat MEST

Compounds of this invention dosed by the oral route as a suspension in methyl cellulose and tested one hour post dosing show an increase in seizure threshold. For example, the product of Example 1 showed a statistically significant increase (225%) when examined in the rat model at a dose of 2 mg/kg p.o.

What is claimed is:

1. A compound of formula (I) or pharmaceutically acceptable salt thereof:

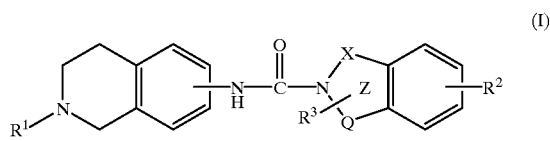

where X and Q are independently a bond, methylene or ethylene groups such the ring structure Z is a five or six membered ring, $R^1$ is hydrogen or $C_{1-6}$ alkyl, $R^2$ is hydrogen or up to four substituents independently selected from halogen, $CF_3$, $NO_2$, CN, $N_3$, $C_{1-6}$ alkylO—, $C_{1-6}$ alkylS—, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3CO$—, $CF_3O$, $C_{1-6}$alkylCO—, $C_{3-6}$cycloalkylCO—, $C_{3-6}$cycloalkyl-$C_{1-4}$alkylCO—, phenyl, phenoxy, benzyloxy, benzoyl, phenyl-$C_{1-4}$alkyl-, or —$NR^4R^5$ where $R^4$ is hydrogen or $C_{1-4}$ alkyl, and $R^5$ is hydrogen, $C_{1-4}$alkyl, —CHO, —$CO_2C_{1-4}$alkyl or —$COC_{1-4}$alkyl, and $R^3$ is hydrogen or up to two $C_{1-6}$ alkyl groups.

2. A compound according to claim 1 which is a carboxylic acid (tetrahydroisoquinolin-5-yl) or (tetrahydroisoquinolin-7-yl) amide.

3. A compound according to claim 1 which is a 3,4-dihydro-1H-isoquinoline or 3,4-dihydro-2H-quinoline or 2,3-dihydroindole N-carboxamide.

4. A compound according to claim 1, in which $R^1$ is hydrogen, methyl, ethyl or propyl, $R^2$ is hydrogen, or one or more of methyl, ethyl, n-butyl, phenyl, iso-propyl, t-butyl, methoxy, ethoxy, n-propoxy, iso-propoxy, n-butoxy, phenoxy, benzyloxy, bromo, chloro, fluoro, iodo, nitro, cyano, acetyl, pivaloyl, iso-butyroyl, benzoyl, iodobenzoyl, trifluoromethyl, trifluoromethoxy, trifluoroacetyl, amino, acetylamino, methylthio, n-propylsulfonyl, iso-propylsulfonyl or dimethylsulfamoyl, and $R^3$ is hydrogen or one or more methyl groups.

5. A compound according to claim 1 which is 2,3-dihydroindole-1-carboxylic acid (2-methyl-1,2,3,4-tetrahydroisoquinolin-7-yl)amide, 3,4-dihydro-1H-isoquinoline-2-carboxylic acid (2-methyl-1,2,3,4-tetrahydriosoquinolin-7-yl)amide, 2,3-dihydro-2H-quinoline-1-carboxylic acid (2-methyl-1,2,3,4-tetrahydroisoquinolin-7-yl)amide, 2,3-dihydro-5-methylthio-6-trifluoromethyl-indole-1-carboxylic acid (2-methyl-1,2,3,4-tetrahydroisoquinolin-5-yl)amide, 2,3-dihydro-6-methoxyindole-1-carboxylic acid (2-methyl-1,2,3,4-tetrahydro-isoquinolin-7-yl)amide, 2,3-dihydro-4-methoxyindole-1-carboxylic acid (2-methyl-1,2,3,4-tetrahydro-isoquinolin-7-yl)amide, 2,3-dihydro-4,5,6,7-tetrafluoroindole-1-carboxylic acid (2-methyl-1,2,3,4tetrahydroisoquinolin-7-yl)amide, 2,3-dihydro-5-fluoroindole-1-carboxylic acid (2-methyl-1,2,3,4-tetrahydro-isoquinolin-7-yl)amide, 2,3-dihydro-5-nitroindole-1-carboxylic acid (2-methyl-1,2,3,4-tetrahydro-isoquinolin-7-yl)amide, 2,3-dihydro-6-nitroindole-1-carboxylic acid (2-methyl-1,2,3,4-tetrahydro-isoquinolin-7-yl)amide, 2,3-dihydro-5-methoxy-6-trifluoromethylindole-1-carboxylic acid (2-methyl-1,2,3,4-tetrahydroisoquinolin-7-yl)amide, 3,3-dimethyl-2,3-dihydroindole-1-carboxylic acid (2-methyl-1,2,3,4-tetrahydro-isoquinolin-7-yl)amide, 2,3-dimethyl-2,3-dihydroindole-1-carboxylic acid (2-methyl-1,2,3,4-tetrahydro-isoquinolin-7-yl)amide, 2,3-dimethyl-2,3-dihydroindole-1-carboxylic acid (2-methyl-1,2,3,4-tetrahydro-isoquinolin-7-yl)amide, or 3,3-dimethyl-5-fluoro-2,3-dihydroindole-1-carboxylic acid (2-methyl-1,2,3,4-tetrahydroisoquinolin-7-yl)amide;

or a pharmaceutically acceptable salt or solvate thereof.

6. A process for the preparation of compounds of formula (I), which comprises reacting a compound of formula (II)

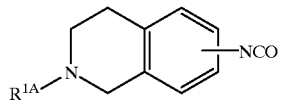

(II)

where $R^{1A}$ is $R^1$ as defined for formula (I) or a group convertible to $R^1$, with a compound of formula (III)

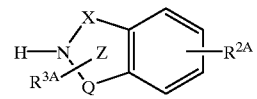

(III)

where X, Q and Z are as defined for formula (I), and $R^{2A}$, $R^{3A}$ are $R^2$, $R^3$ as defined for formula (I) or a group or groups convertible to $R^2$, $R^3$ and where required converting a $R^{1A}$, $R^{2A}$ or $R^{3A}$ group to a $R^1$, $R^2$ or $R^3$ group, converting one $R^1$, $R^2$ or $R^3$ group to another $R^1$, $R^2$ or $R^3$ group, converting a salt product to the free base or another salt which is pharmaceutically acceptable, or converting a free base product to a pharmaceutically acceptable salt.

7. A pharmaceutical composition for use in the treatment and/or prophylaxis of disorders treatable and/or preventable with anti-convulsive agents, epilepsy, post-traumatic epilepsy, migraine, neuralgia, trigeminal neuralgia, neuropathic pain, dental pain, cancer pain, which comprises a compound of formula (I), or a pharmaceutically acceptable salt or solvate thereof, and a pharmaceutically acceptable carrier.

8. A method of treatment and/or prophylaxis of disorders treatable and/or preventable with anti-convulsive agents, epilepsy, post-traumatic epilepsy, migraine, neuralgia, trigeminal neuralgia, neuropathic pain, dental pain, cancer pain, comprising administering to the sufferer in need thereof an effective or prophylactic amount of a compound of formula (I), or a pharmaceutically acceptable salt or solvate thereof.

* * * * *